United States Patent [19]
Li

[11] Patent Number: 6,063,036
[45] Date of Patent: May 16, 2000

[54] PORTABLE ALARM APPARATUS FOR SUDDEN HEART ATTACK PATIENT

[76] Inventor: Pao-Lang Li, 532, Min-Tzwu Rd. Lu Chou Hsiang, Taipei, Taiwan

[21] Appl. No.: 09/085,449

[22] Filed: May 28, 1998

Related U.S. Application Data

[63] Continuation-in-part of application No. 09/025,798, Feb. 19, 1998.

[51] Int. Cl.⁷ ....................................................... A61N 5/00
[52] U.S. Cl. ............................................ 600/503; 600/500
[58] Field of Search ..................................... 600/481–503, 600/504; 128/897–898

[56] References Cited

U.S. PATENT DOCUMENTS

| | | | |
|---|---|---|---|
| 3,361,128 | 1/1968 | Colman | 600/500 |
| 3,972,320 | 8/1976 | Kalman | 600/503 |
| 4,088,138 | 5/1978 | Diack et al. | 600/503 |
| 4,151,831 | 5/1979 | Lester | 600/503 |
| 4,256,117 | 3/1981 | Percia et al. | 128/690 |
| 4,662,378 | 5/1987 | Thomis | 600/508 |
| 5,074,309 | 12/1991 | Gerdt | 600/500 |
| 5,090,408 | 2/1992 | Spofford et al. | 128/207.14 |
| 5,691,932 | 11/1997 | Reiner et al. | 600/503 |

*Primary Examiner*—Cary O'Connor
*Assistant Examiner*—Michael Astorino
*Attorney, Agent, or Firm*—Rosenberg, Klein & Lee

[57] ABSTRACT

A portable alarm apparatus for use by a sudden heart attack patient is provided that is characterized by a housing part connected to a suspension member for hanging around a patient's neck. Sensors are disposed on the suspension member and connected to an extending lead, enabling the sensors to contact respective pulse spots on the patient's neck, due to the downward force resulting from gravity acting on the housing part. The sensors detect the pulse signals in an artery in the user's neck corresponding to heartbeats and output an electrical signal for input to a control circuit disposed in the housing part for storage, display and generation of a warning alarm.

2 Claims, 7 Drawing Sheets

PORTABLE ALARM APPARATUS FOR SUDDEN HEART ATTACK PATIENT

The present invention is a continuation-in-part application of an earlier application, Ser. No. 09/025,798, filed Feb. 19, 1998 now in pendency referring to an alarm apparatus fastened at inside wrist to sense the pulse on wrist and generate warning alarm or phonetic sound asking for help when the heartbeats of a patient reach an endangering limit predetermined to avoid any delay for sending to hospital.

BACKGROUND OF THE INVENTION

1. Field of the Invention

The present invention is particularly characterized by connecting the alarm apparatus with a suspension member to detect pulse on the patient's neck.

2. Description of the Related Arts

According to the alarm apparatus (1) of the prior application, shown in FIG. 5 to FIG. 7, which is connected with an integral control circuit and disposed in a housing part (2), like a wrist watch, fastened to inside of wrist (4) by a fastening belt (3), and detect the pulse from the wrist (4) by a sensor (5) set on the back side of said housing part (2), showing practical heartbeats per minute on a display screen (7) of a display device (6) in the front for user's observation. Wherein the patient's pulse is detected from the wrist (4) and then conveyed into the housing part (2), converted to electronic signal by energy transducer (8); electric pulse is formed by an oscillating circuit (9) at a pre-set frequency, then is counted through the energy transducer (8) and oscillating circuit (9) once the pulse is detected. Lastly, by a counter circuit (28) the electric pulse is converted to form of speed of pulse, showed by three-digit number on the display screen (7) of the display device (6) representing the pulse per minute for user's observation. Along one lateral of the housing part (2) are start button (10), maximum button (11), and minimum button (12). In which the start button (10) refers to a button to start the integral circuit operation; one minute after pressing said start button (10) user's heartbeats begin to reveal every minute. Said maximum button (11) refers to a button which is pressed to record a pulse maximum limit by releasing said button (11) after setting limit numbers on the display screen (7) the pulse number is saved in the recorder of the internal pre-set circuit (13) for comparison with the detected pulse in an internal comparator (14) which may trigger an internal alarm (15) once the patient's detected pulse is equal to or higher than the pre-set maximum limit to generate alarm signal, which may be alarm sound or phonetic sound, for the patient's or nurse's attention to take necessary actions. Said minimum button (12) refers to a button for recording a pulse minimum limit in accordance with the patient's condition, having same pre-set process with said maximum button (11), the pulse minimum limit is saved in the recorder of the internal pre-set circuit (13) for comparison with the detected pulse in said internal comparator (14) which may trigger the alarm (15) once the patient's detected pulse is equal or lower than the pre-set minimum limit to generate alarm signal warning the patient or nurse to take necessary actions.

SUMMARY OF THE INVENTION

The main object of the present invention is to connect the alarm apparatus disclosed in the prior application with a suspension member for detecting the patient's pulse in a more accurate way since neck part has denser pulse spots for detection. These and other objects structure and advantages of the invention are depicted in the drawings and will be explained in the following.

DETAILED DESCRIPTION OF THE INVENTION

Figure 7:
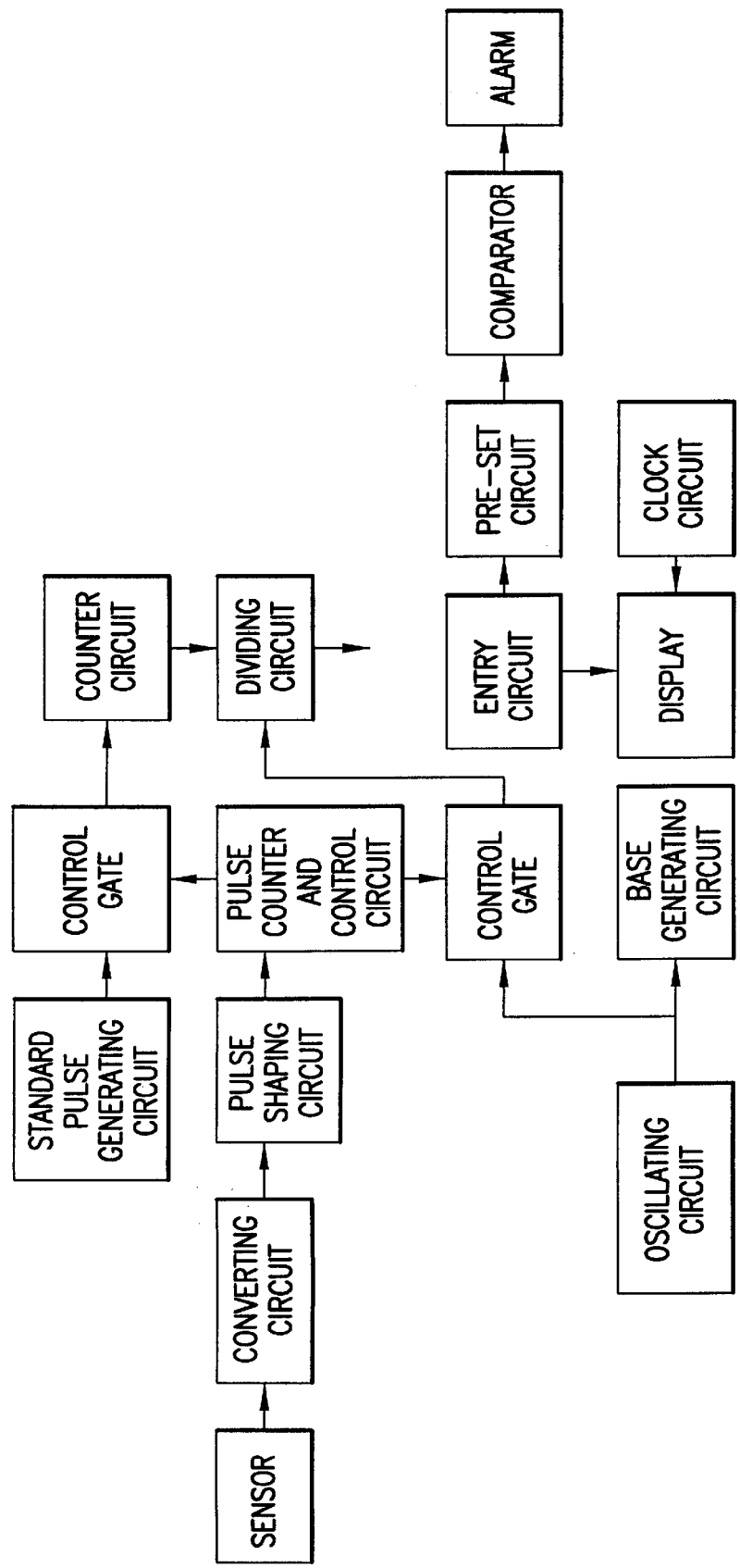
FIG. 7 is the inner circuit block of the alarm apparatus in FIG. 5.
Figure 8:
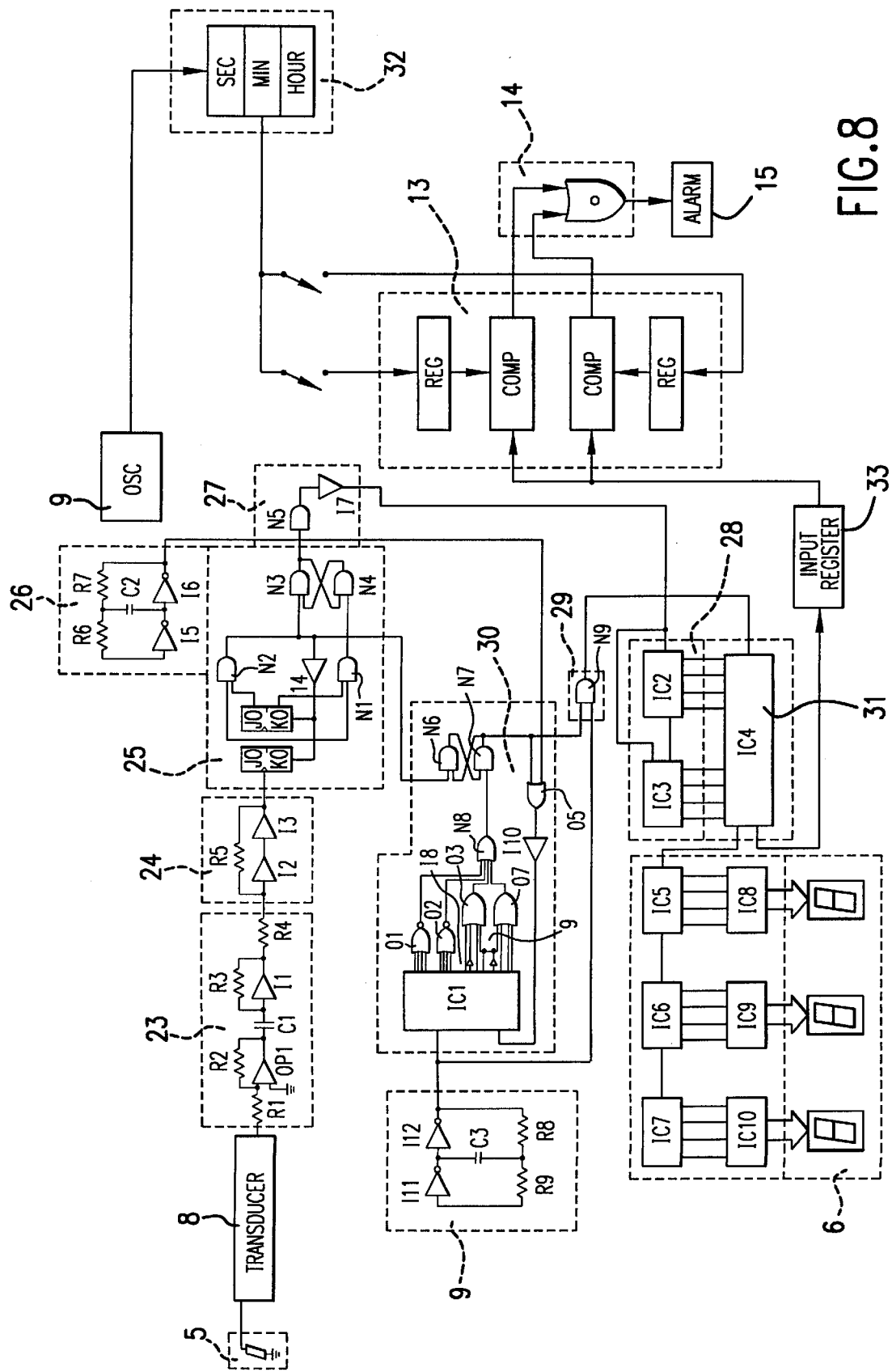
FIG. 8 is the circuit diagram of the alarm apparatus in FIG. 5.

Now refers to FIG. 7 and FIG. 8 showing the internal circuit of the present invention, wherein a sensor (5) is a device for detecting the pumping press of artery in the wrist (4) and converting the beats to electric signal amplified by a signal amplifier (23) to a degree being able to be digitized by a squaring circuit (24) and shaped as square pulse for counting in a pulse counter and control circuit (25) generating a control signal during entering a first and third pulse for control gate (27) which converts pulse time to a base and gate (29) which controls the entrance of the pulse number converted from an oscillating circuit (9) to a 1200 base generating circuit (30) into a dividing circuit (31). In order to enhance the accuracy of detection, a standard pulse generating circuit (26) is disposed to amplify the time of two pulses by 10 times, then the amplified time is converted to a base in the control gate (27) as a divisor saved temporarily in a bit counter (28) to divide base 1200 generated from the base generating circuit (30) in the dividing circuit (31) resulting in a number representing the pulse number per minute.

Figure 1:
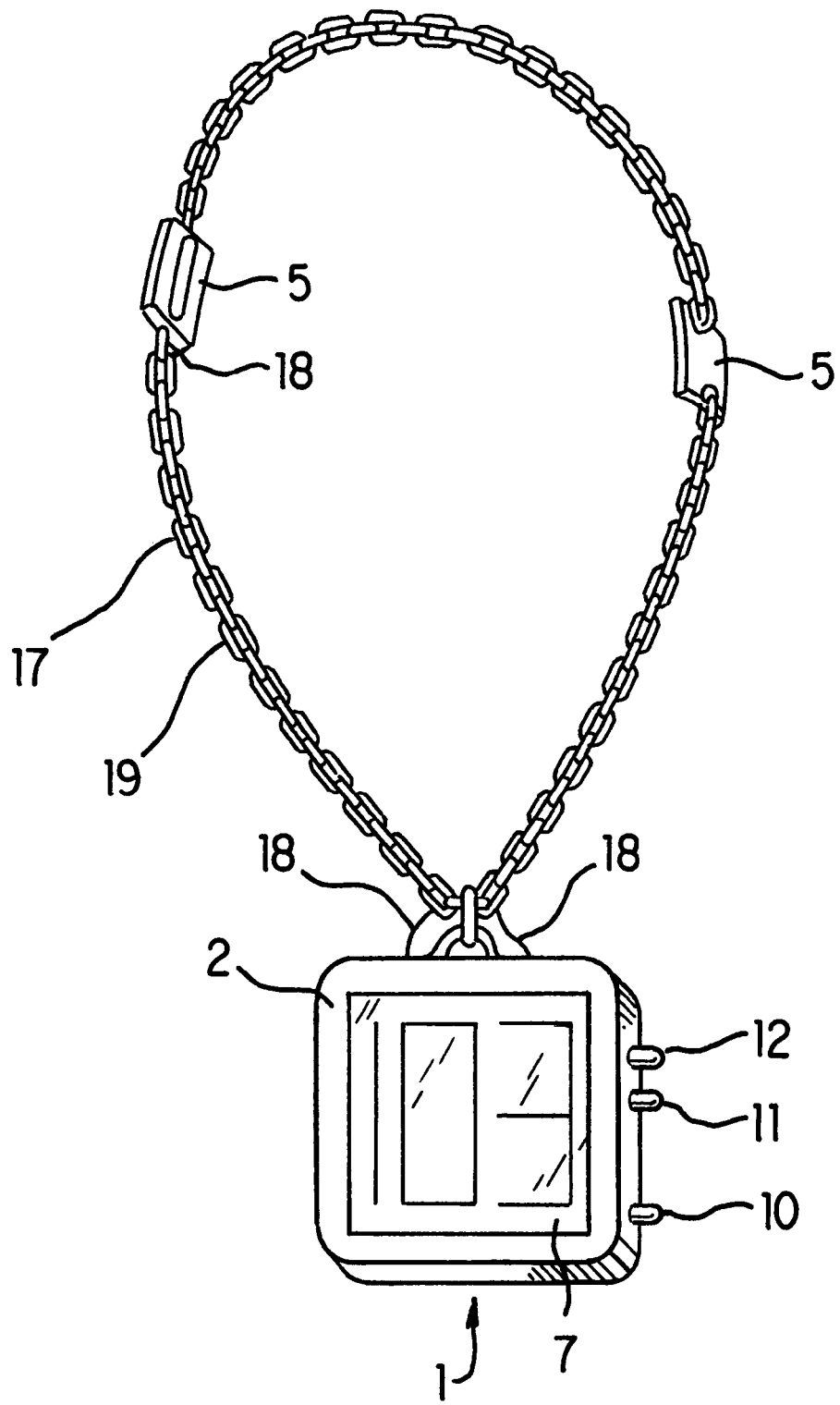
FIG. 1 shows the first embodiment of this invention.
Figure 2:
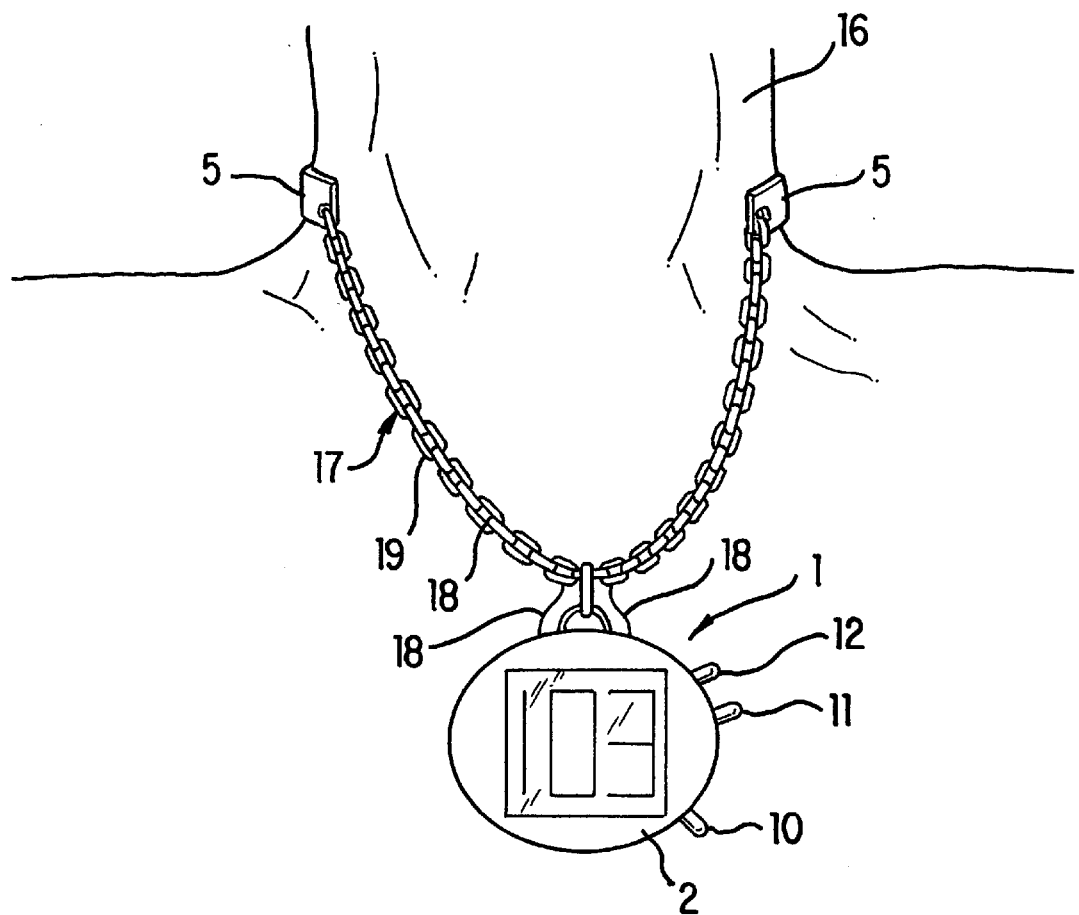
FIG. 2 shows the using state of FIG. 1.

Further refers to FIGS. 1, 2, and 7, showing a first embodiment of alarm apparatus (1) connected with an integral control circuit and disposed in a housing part (2) showing practical heartbeats per minute by three-digit number on a display screen (7) in the front, and along one lateral of the housing part (2) of the present invention are start button (10), maximum button (11), and minimum button (12). In which the stat button (10) refers to a button to start the integral circuit operation. The maximum button (11) and minimum button (12) on said housing part (2) are for recording and saving both pulse maximum and minimum limit in a recorder of an internal pre-set circuit (13) for comparison of the detected pulse to pre-set maximum and minimum in an internal comparator (14) and trigger an internal alarm (15) to generate alarm signal when the patient's practical pulse is equal to or higher than the maximum limit and equal to or lower than the minimum limit. Said housing part (2) has one lateral connected with one end of a suspension member (17) for hanging on patient's neck (16), and extending lead (18) for contact with sensors (5) disposed on the suspension member (17); with gravity of the housing part (1) of the alarm apparatus (1), the housing part (2) hangs down at patient's frontal chest and the sensors (5) on the suspension member (17) tightenedly contacts patients neck (16) to detect patient's pulse from the neck part (16) and convey the heart beats signal into the housing part (2) by said lead (18) for procession, display, and generate warning alarm when patient's heartbeats appears unstable (equal to or higher than pre-set maximum limit and equal to or lower than pre-set minimum limit). The suspension member (17) in this embodiment refers to a necklace (19) linked with metal rings, and the housing part (2) is preferable to arrange various adornment in addition to the display screen (7).

Figure 3:
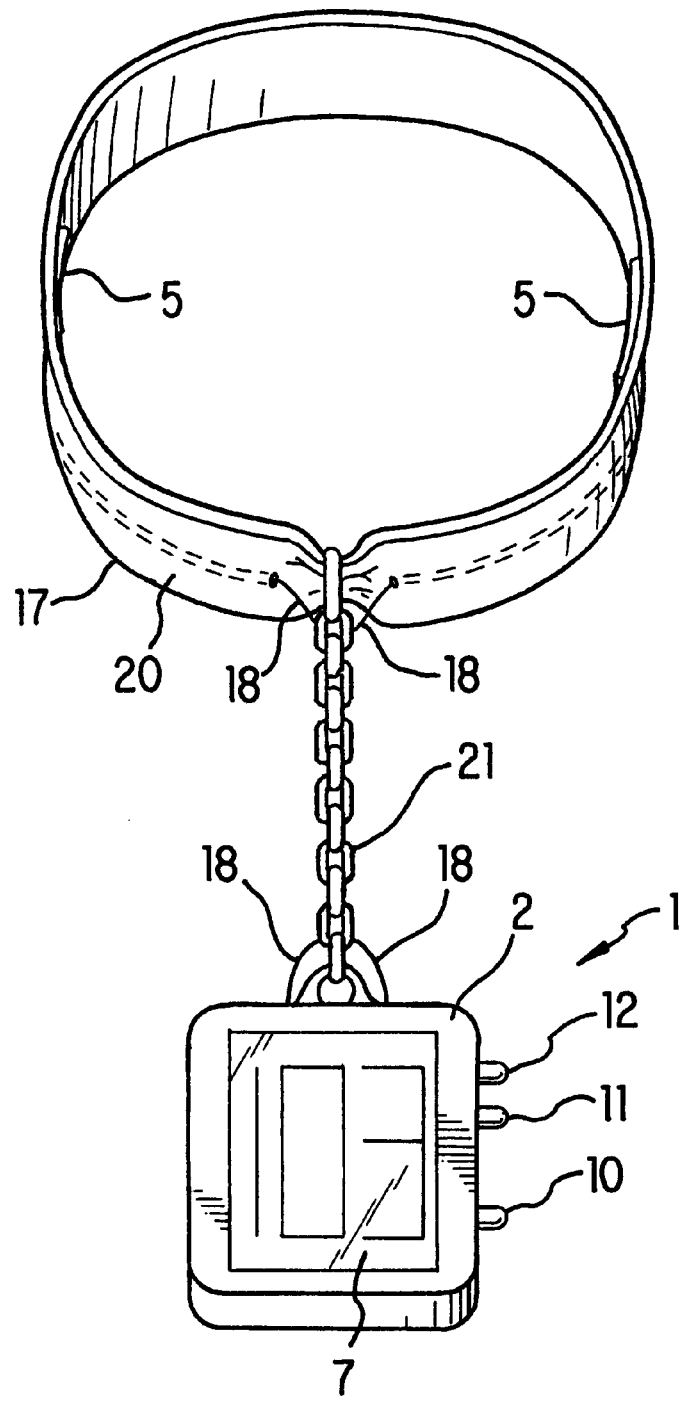
FIG. 3 shows the second embodiment of this invention.

As shown in FIG. 3, the suspension member (17) is also preferable composed of a belt (20) with slight flexibility and a section of chain (21), enabling the sensors (5) connected with the belt (20) to contact corresponding pulse spots on neck (16).

Figure 4:
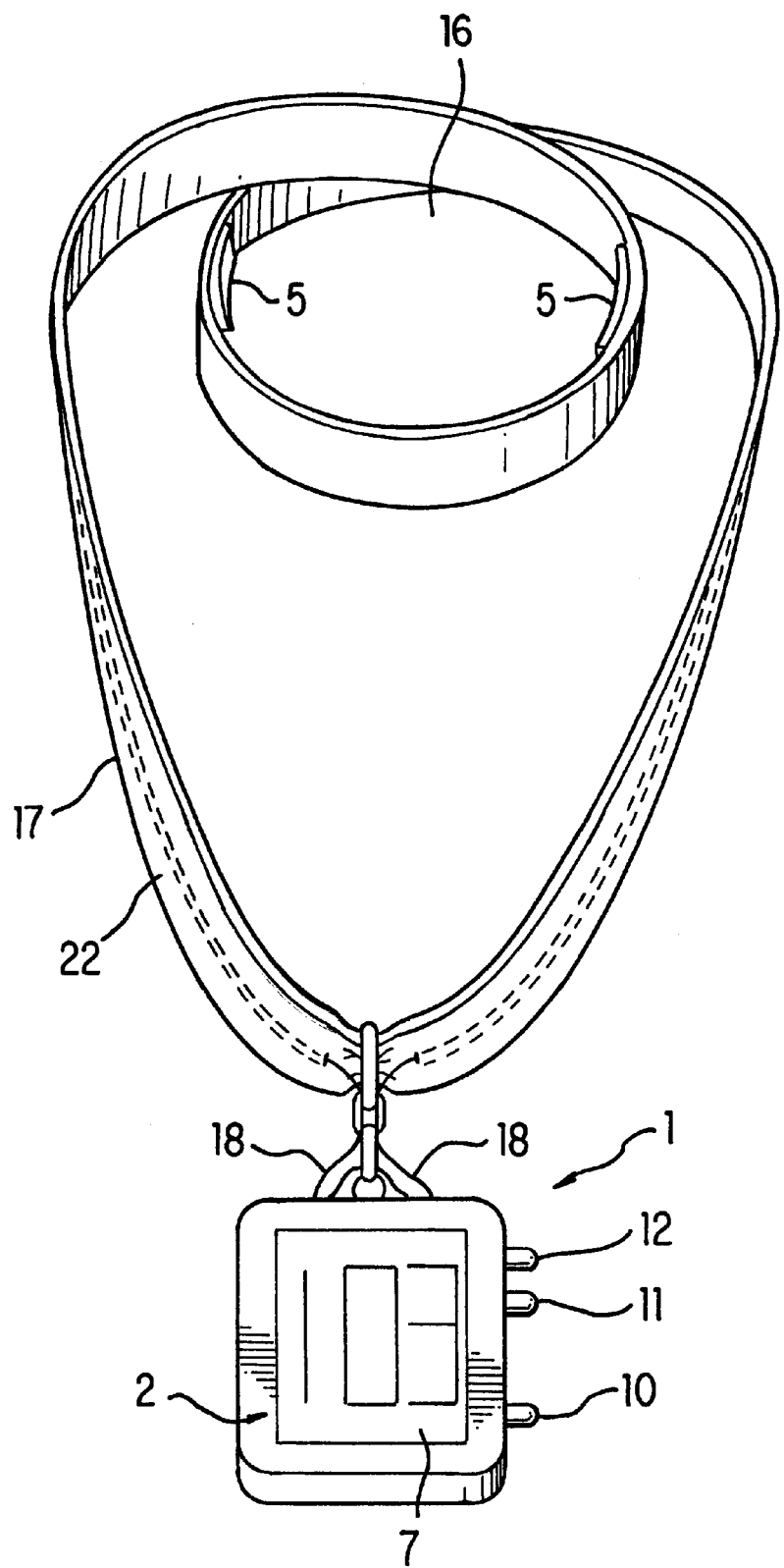
FIG. 4 shows the third embodiment of this invention.
Figure 5:
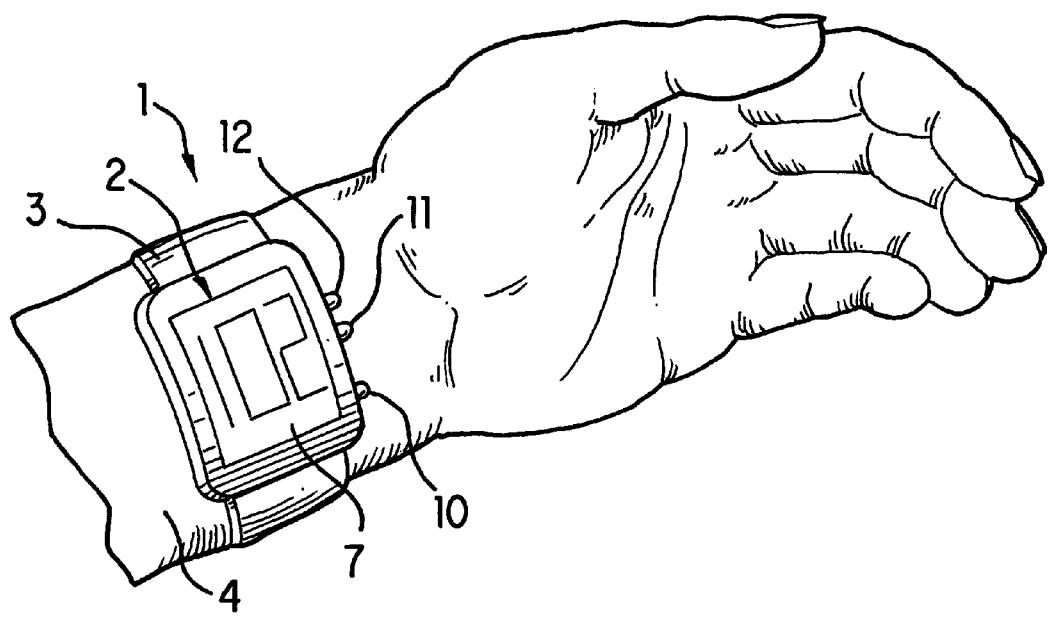
FIG. 5 shows the front view of the first application of alarm apparatus being worn on wrist.
Figure 6:
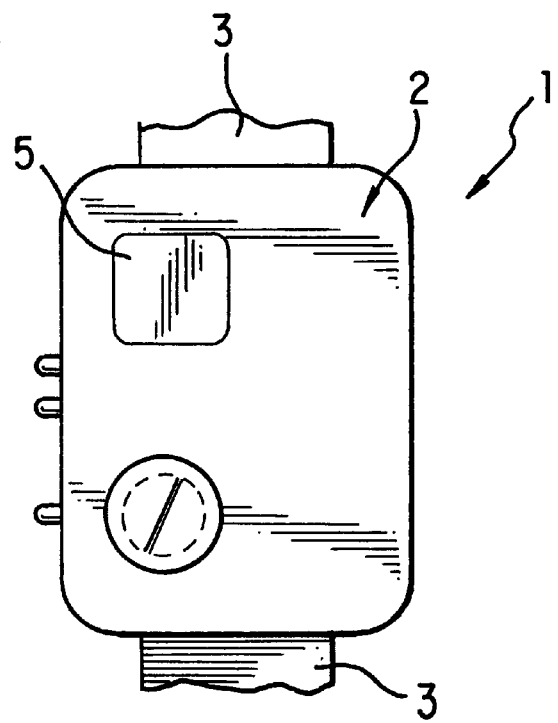
FIG. 6 shows rear view of the alarm apparatus in FIG. 5.

As shown in FIG. 4, the suspension member (17) is possible a soft belt (22) with sufficient length for making a loop around the neck (16) and then hangs down enabling the sensors (5) on the belt (22) to contact pulse spots on patient's neck (16) by gravity of the alarm apparatus(1).

I claim:

1. A portable alarm apparatus for a sudden heart attack patient, comprising:

a housing having a predetermined weight, said housing having a frontal display screen for displaying a pulse rate thereon;

suspension means coupled to said housing for hanging said housing around a user's neck, said suspension means including a suspension member and at least one sensor for sensing pressure changes and outputting an electrical signal responsive thereto, said sensor being positioned on the user's neck for detecting pulse pressure changes therein when said suspension member is positioned about the user's neck, said sensor being adapted to be in contiguous contact with the user's neck by a force provided by said predetermined weight of said housing transmitted through said suspension member;

a control circuit disposed within said housing and having (a) an input coupled to said sensor for receiving said electrical signal, (b) means for determining a heart rate from said electrical signal, (c) an output coupled to said display screen for displaying said determined heart rate, (d) means for input and storage of a maximum heart rate value and a minimum heart rate value, (e) means for comparing said stored maximum and minimum heart rate values with said determined heart rate coupled to said input and storage means, and (f) means for output of an alarm signal coupled to said comparing means, said alarm signal being output responsive to said determined heart rate being greater than said stored maximum heart rate value, and in the alternative responsive to said determined heart rate being lower than stored minimum heart rate value.

2. The portable alarm apparatus as recited in claim 1, wherein said suspension means includes a plurality of said sensors displaced one from the other along said suspension member.

* * * * *